US012661010B2

(12) United States Patent
Wittner et al.

(10) Patent No.: US 12,661,010 B2
(45) Date of Patent: Jun. 23, 2026

(54) SPECTROSCOPY USING TIME-RESOLVED ELASTIC AND RAMAN SCATTERING

(71) Applicant: Liom Health AG, Pfäffikon (CH)

(72) Inventors: Bernd Wittner, Pfäffikon (CH); Jean-Christophe Blancon, Galgenen (CH); Paolo Livi, Birmensdorf (CH)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 60 days.

(21) Appl. No.: 18/291,059

(22) PCT Filed: Jul. 22, 2021

(86) PCT No.: PCT/EP2021/070530
§ 371 (c)(1),
(2) Date: Jan. 22, 2024

(87) PCT Pub. No.: WO2023/001377
PCT Pub. Date: Jan. 26, 2023

(65) Prior Publication Data
US 2024/0324880 A1 Oct. 3, 2024

(51) Int. Cl.
*A61B 5/00* (2006.01)
*A61B 5/01* (2006.01)
(Continued)

(52) U.S. Cl.
CPC .............. *A61B 5/0075* (2013.01); *A61B 5/01* (2013.01); *A61B 5/14546* (2013.01); *A61B 5/1455* (2013.01); *A61B 5/443* (2013.01)

(58) Field of Classification Search
CPC .............................. A61B 5/0075; A61B 5/443
See application file for complete search history.

(56) References Cited

U.S. PATENT DOCUMENTS

| | | | |
|---|---|---|---|
| 5,919,140 A | 7/1999 | Perelman et al. | |
| 6,070,583 A | 6/2000 | Perelman et al. | |
| (Continued) | | | |

FOREIGN PATENT DOCUMENTS

| | | | |
|---|---|---|---|
| WO | 2020201156 A1 | 10/2020 | |
| WO | 2021116766 A1 | 6/2021 | |

OTHER PUBLICATIONS

Alessandro Torricelli et al., "Time domain functional NIRS imaging for human brain mapping", Jun. 5, 2013, 28 pages.
(Continued)

*Primary Examiner* — Colin T. Sakamoto
(74) *Attorney, Agent, or Firm* — Mannava & Kang, P.C.

(57) ABSTRACT

A method for the spatially-resolved probing of bio logical tissue (102) comprises the steps of emitting, by means of at least one light source (106), a series of light pulses into the tissue and of measuring, by means of a plurality of light detectors (108), a plurality of time-resolved responses to the light pulses scattered from the tissue. The measurement is carried out with a temporal resolution better than 20 ps. A plurality of first responses is in response to light pulses at a first illumination band and is measured at a plurality of first detection bands. The first detection bands differ from each other and from the first illumination band in order to detect inelastic scattering. A plurality of second responses is in response to light pulses at a second illumination band and is measured at a second detection band. The second detection band overlaps with the second illumination band in order to detect elastic scatting. Time of flight analysis of both responses allows to e.g. use elastic scattering for locating structures (S1, S2, S3) in the tissue (102) and for assigning them to the inelastic scattering data.

13 Claims, 4 Drawing Sheets

(51) Int. Cl.
    *A61B 5/145*         (2006.01)
    *A61B 5/1455*      (2006.01)

(56)             References Cited

U.S. PATENT DOCUMENTS

| | | |
|---|---|---|
| 7,831,061 B1 | 11/2010 | Lubard et al. |
| 11,035,797 B2 | 6/2021 | Yang et al. |
| 2012/0010477 A1 | 1/2012 | Amano et al. |
| 2012/0203114 A1 | 8/2012 | Bechtel et al. |
| 2016/0370228 A1 | 12/2016 | Tok et al. |
| 2020/0345234 A1 | 11/2020 | Li et al. |
| 2021/0010865 A1 | 1/2021 | Yang et al. |

OTHER PUBLICATIONS

Dan Fu et al., "High-resolution in vivo imaging of blood vessels without labeling", Sep. 15, 2007, Vo. 32, No. 18, Optics Letters, pp. 2641-2643.

Enrico Conca et al., "Large-Area, Fast-Gated Digital SiPM with Integrated TDC for Portable and Wearable Time-Domain NIRS", in IEEE Journal of Solid-State Circuits, vol. 55, No. 11, pp. 3097-3111, Nov. 2020.

Ingeborg E. Iping et al., "Time-resolved spatially offset Raman spectroscopy for depth analysis of diffusely scattering layers", Oct. 13, 2010, 5 pages.

Jeon Woong Kang et al., "Direct observation of glucose fingerprint using in vivo Raman spectroscopy", Science Advances, Research Article, Applied Sciences and Engineering, Jan. 24, 2020, 8 pages.

Jun Wu et al., "Three-dimensional imaging of objects embedded in turbid media with fluorescence and Raman spectroscopy", Jun. 20, 1995, vol. 34, No. 18, Applied Optics, pp. 3425-3430.

Martin Wolf et al., "Imaging oxygenation by near-infrared optical tomography based on SPAD image sensors", International SPAD Sensor Workshop Jun. 8, 2020, 41 pages.

Meha Qassem et al., "Review of Modern Techniques for the Assessment of Skin Hydration", Cosmetics Mar. 9, 2019, 28 pages.

Michele Lacerenza et al., "Wearable and wireless time-domain near-infrared spectroscopy system for brain and muscle hemodynamic monitoring", Biomedical Optics Express, Vo. 11, No. 10/ Oct. 1, 2020, pp. 5934-5949.

Prajokta Ray et al., "Label-Free Optical Detection of Multiple Biomarkers in Sweat, Plasma, Urine, and Saliva", ACS Sensors, 2019, 4, pp. 1346-1357.

Saeed Samaei et al., "Time-domain diffuse correlation spectroscopy (TD-DCS) for noninvasive, depth-dependent blood flow quantification in human tissue in vivo", Nature Research, Scientific Reports, (Year 2021), 10 pages.

Sara Mosca et al., "Spatially offset Raman spectroscopy", Nature Reviews/Methods Primers, Year 2021, 16 pages.

Sara Mosca et al., "Spatially Offset Raman Spectroscopy-How Deep?", Analytical Chemistry, 2021, 93, pp. 655-6762.

Tom Lister et al., "Optical properties of human skin", Journal of Biomedical Optics, 17(9), 090901 (Sep. 2012, 16 pages.

Wuwei Ren et al., "Multimodal imaging combining time-domain near-infrared optical tomography and continuous-wave fluorescence molecular tomography", Optics Express, vol. 28, No. 7/ Mar. 30, 2020, pp. 9860-9874.

Zhiwei Huang et al., "Raman spectroscopy of in vivo cutaneous melanin", Journal of Biomedical Optics 9(6), pp. 1198-1205 (Nov./ Dec. 2004).

International Search Report and Written Opinion for Application No. PCT/EP2021/070530, mailed Apr. 20, 2022, 8 pages.

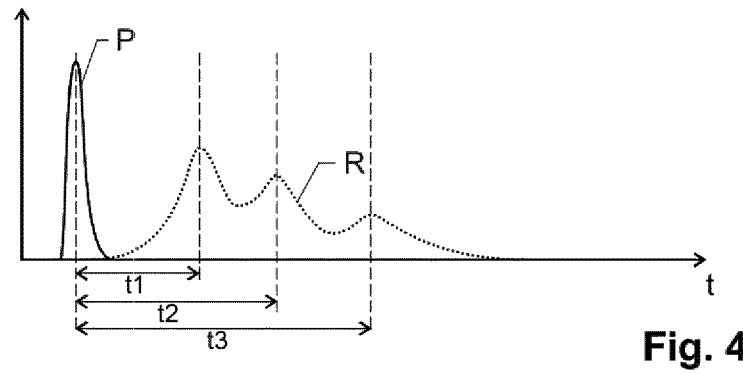
Fig. 4
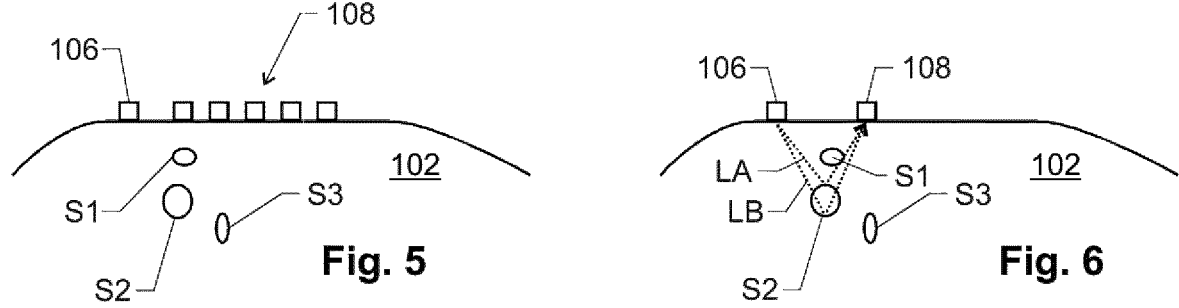
Fig. 5
Fig. 6
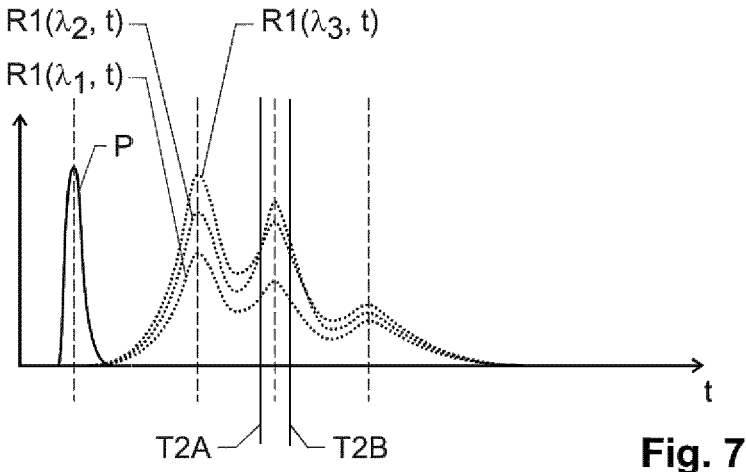
Fig. 7

SPECTROSCOPY USING TIME-RESOLVED ELASTIC AND RAMAN SCATTERING

CLAIM FOR PRIORITY

The present application is a national stage filing under 35 U.S.C 371 of PCT application number PCT/EP2021/070530, having an international filing date of Jul. 22, 2021, the disclosure of which is hereby incorporated by reference in its entirety.

TECHNICAL FIELD

The invention relates to a method for the spatially-resolved probing of biological tissues as well as to a device for performing this method.

BACKGROUND ART

Torricelli et al. in NeuroImage 85 (2014) 28-50 (http://doi.org/10.1016/j.neuroimage.2013.05.106) describe a time-domain function NIRS imaging technique. It is based on sending short light pulses into the tissue and on time-correlated single photon counting to measure a time-resolved response.

Further, it has been known to probe biological tissues using spatially offset Raman spectroscopy, see. e.g. Mosca et al. in Anal. Chem. 2021, 93, 6755-6762 (https://doi.org/10.1021/acs.analchem.1c00490).

Iping Petterson et al, in Analyst, 135, 3255-3259 (2010) (https://doi.org/10.1039/C0AN00611D) describe time-resolved Raman spectroscopy for a depth-resolved analysis of biomedical applications.

DISCLOSURE OF THE INVENTION

The problem to be solved by the present invention is to provide a method and a device of the type mentioned above that allows to obtain rich, spatially-resolved information about a biological tissue.

This problem is solved by the method and device of the independent claims.

Accordingly, the method for the spatially-resolved probing of biological tissues comprises at least the following steps:

Emitting, by means of at least one light source, a series of light pulses: These light pulses are sent into the tissue to be scattered there.

Measuring, by means of a plurality of light detectors, a plurality of time-resolved scattering responses to the light pulses coming back from the tissue. The measurements have a temporal resolution better than 40 ps. The responses include at least the following:

a) A plurality of first responses is measured in response to light pulses in a first illumination band (with the term "band" referring to a spectral band, i.e. a wavelength range). These measurements are made at a plurality of first detection bands. The first detection bands differ from each other and from the first illumination band. Hence, the first plurality of responses are caused by inelastic scattering (Raman scattering) in the tissue.

b) A second plurality of responses is measured in response to light pulses in a second illumination band, which second illumination band may or may not be the same as the first illumination band. These measurements are carried at a second detection band. The second detection band overlaps with the second illumination band.

Hence, the second plurality of responses are caused by elastic scattering in the tissue. Advantageously, the term "overlap with" is understood such that the peak illumination wavelength of the light pulses lies within the full width at half maximum of the second spectral detection band.

Using a temporal resolution of better (smaller) than 40 ps allows to spatially resolve specific tissue regions that have scattered the light pulses with a resolution of a few millimeters. Advantageously, the temporal resolution is even better (smaller) than 20 ps, in particular better than 10 ps.

The method combines the first and second responses for deriving spatially-resolved information on the tissue.

This method combines temporally resolved measurements of inelastic Raman scattering (as obtained from the first responses) and elastic scattering (as obtained from the second responses). This combination is advantageous because the first and second responses contain complementary information that can be combined for a better understanding of the tissue. For example:

Raman scattering (i.e. the first responses) allows to recognize substances that are hard or impossible to identify by means of elastic scattering alone, and vice versa. For example, glucose and lactate can be easily identified from Raman measurements while blood oxygenation is best detected using elastic scattering.

Elastic scattering (i.e. the second responses) provides a much better signal-to-noise ratio than Raman scattering, and it therefore allows to detect and identify the structures (such as veins or dermal/subdermal layers with more accuracy, which then can be exploited for a better interpretation of the Raman data (i.e. the first responses).

Advantageously, for good Raman spectroscopy resolution, the first illumination band has a full width at half maximum (FWHM) of less than 5 nm, in particular of less than 1 nm. In addition or alternatively thereto, each of the first spectral detection bands may have a full width at half maximum (FWHM) of less than 5 nm, in particular of less than 2 nm, in particular of less than 1 nm. In particular, FWHM of the first illumination band is less than 1 nm and FWHMs of the first detection bands are less than 1 nm.

Spatial resolution improves when the light source and the detectors are close to each other. Hence, advantageously, the distances between the light source and the light detectors are advantageously less than 20 mm, in particular less than 5 mm.

In an advantageous embodiment, each of at least some of the detectors comprise a single-photon avalanche diode (SPAD) and an optical filter. The optical filter may e.g. be at least one of a multi-layer interference filter or a diffractive grating filter.

The method advantageously involves the step of deriving at least one spatially resolved tissue parameter from combining the first and the second responses. In other words, the tissue parameter is a function of the first as well as of the second responses. The parameter is spatially resolved in the sense that it is attributed to a sub-volume of the tissue.

The tissue is advantageously a body surface of a (human or non-human) animal. In this case, the method may comprise the steps of Sending the light pulses through a skin layer of the animal; and Receiving the first and second responses through the skin layer.

In other words, the method is applied transdermally or transcutaneously, e.g. by means of a wearable device applied to the skin.

The invention also relates to a device for carrying out the method. This device comprises at least the following elements:

At least one light source: There may be several such light sources having different center illumination wavelengths.

A plurality of light detectors: The light detectors are provided for measuring the time-resolved responses from the tissue.

A control unit: The control unit controls the elements of the device and operates them to carry out the measurements.

The device is adapted and structured to perform at least the following steps:

Emitting, by means of the at least one light source, a series of light pulses into the tissue;

Measuring, by means of the plurality of light detectors, a plurality of time-resolved responses to the light pulses scattered from the tissue with a temporal resolution better than 20 ps, wherein a) A plurality of first responses is in response to light pulses at a first illumination band and is measured at a plurality of first detection bands, wherein the first detection bands differ from each other and from the first illumination band; and b) A plurality of second responses is in response light pulses at a second illumination band and is measured at a second detection band, wherein the second detection band overlaps with the second illumination band; and Advantageously, at least some of the detectors comprise a single-photon avalanche diode and an optical filter.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 4 shows a light pulse P a response R as a function of time, FIG. 5 illustrates the imaging of structures in the tissue by means of a light source and several light detectors, FIG. 6 illustrates how to assign a peak in a response to a structure in the tissue, FIG. 7 shows a set of first responses at different wavelengths for several scattering structures.

4

MODES FOR CARRYING OUT THE INVENTION

Overview

Figure 1:
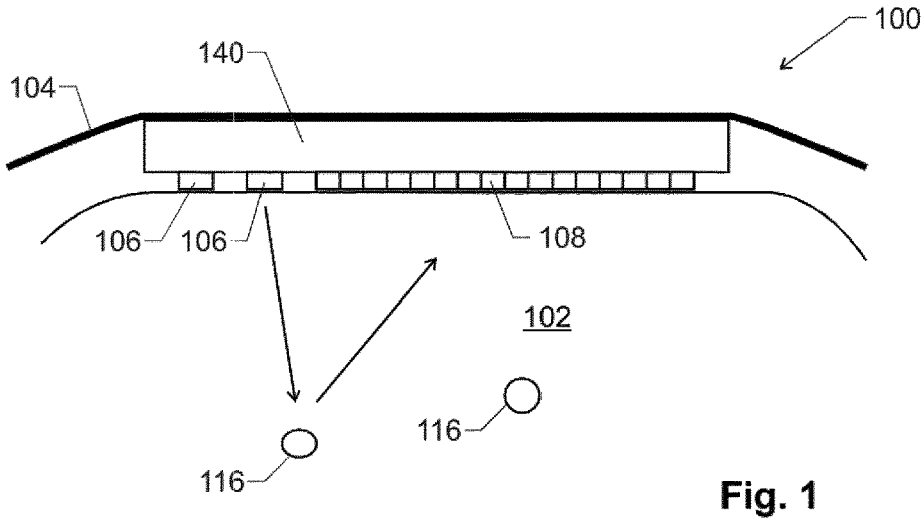
FIG. 1 shows a schematic view of a device placed on skin tissue.
Figure 2:
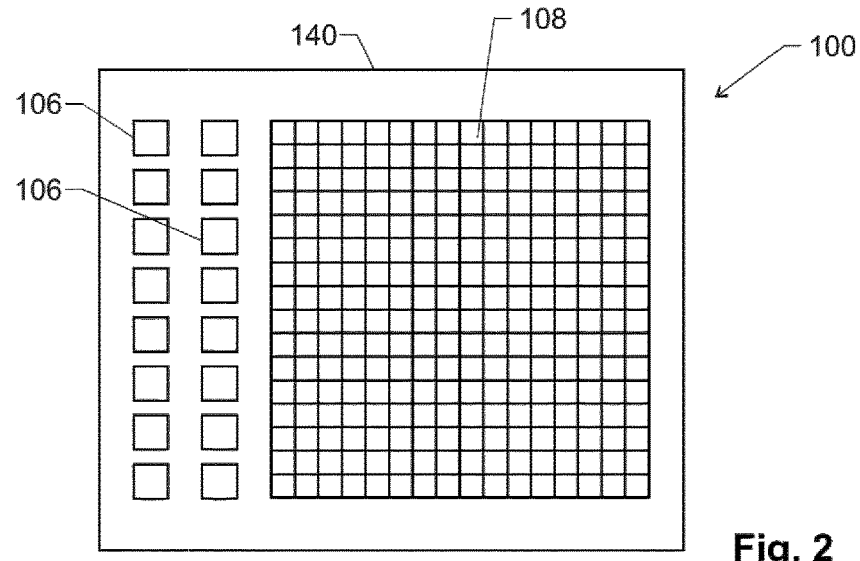
FIG. 2 shows a schematic bottom view of the device (i.e. from the side of the tissue)

FIGS. 1 and 2 show the embodiment of a device 100 located on tissue 102. Tissue 102 may be the skin tissue of a human, and the device may e.g. be a wearable device equipped with a suitable band 104 for affixing it to the body.

Device 100 comprises a plurality of light sources 106 and light detectors 108.

The light sources 106 advantageously comprise at least one laser and/or LED. At least some of the light sources 106 are narrow-band light sources having a spectral width (FWHM) of less than 5 nm, in particular of less than 1 nm, for the reasons outlined above. Advantageously, such light sources are semiconductor lasers.

Depending on applications, the light sources may e.g. be adapted to emit light at at least one wavelength between 350 and 1700 nm.

As shown, there may be several light sources 106 having different center wavelengths.

The light sources 106 are operated to emit short pulses, in particular pulses of a length of less than 100 ps, in particular less than 50 ps.

The light detectors 108 advantageously comprise photodiodes with high sensitivity, such as single-photon-avalanche-diodes (SPADs). There is a plurality of light detectors 108 for different wavelengths.

Advantageously, at least some of the light detectors 108 are narrowband light detectors having a spectral width (FWHM) of less than 5 nm, in particular of less than 2 nm, in particular of less than 1 nm for the reasons outlined above.

The light detectors 108 have a high temporal resolution, i.e. a resolution better than 40 ps, advantageously better than 20 ps, in particular better than 10 ps.

There are several light detectors 108, and they have different center wavelengths (detection bands). These center wavelengths may e.g. be in a wavelength range somewhere between 300 and 1700 nm.

As can be seen, the light sources 106 and the light detectors 108 are advantageously mechanically coupled in order to have a defined spatial relationship, which allows to gain a better understanding of the location of the various scattering centers in the tissue 102.

As mentioned above, the light sources 106 and light detectors 108 are advantageously close to each other for better spatial resolution.

The light sources 106 and the light detectors 108 may be arranged on the same semiconductor chip.

Figure 3:
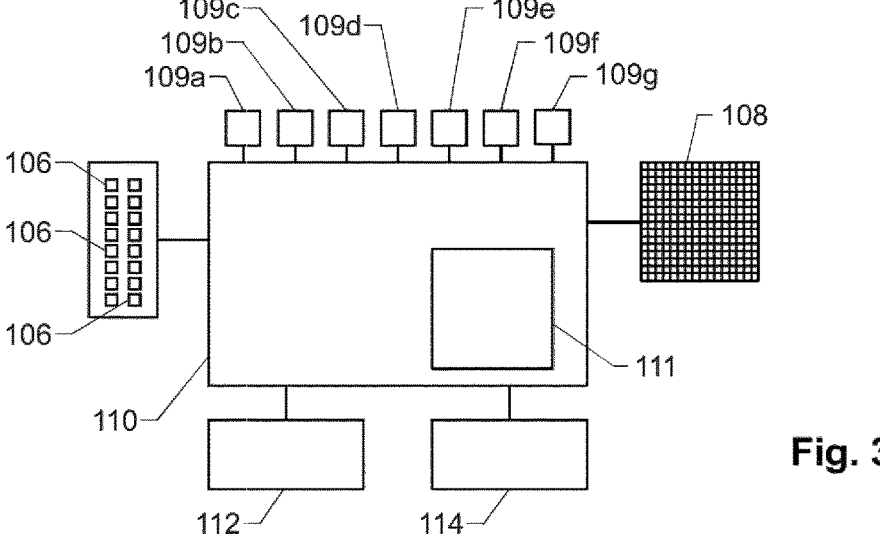
FIG. 3 is a block circuit diagram of some of the components of the device.

FIG. 3 shows a block diagram of the device 100. It comprises a control unit 110, which may e.g. include an ASIC, a microprocessor, and/or FPGA circuitry. It operates the light sources 106 as well as the light detectors 108. It may be connected to further circuitry, such as a display 112 for displaying information to a user and/or to a digital interface 114 for connecting it with a remote computer device.

Advantageously, the components of FIG. 3 are arranged on a single chip.

In operation, control unit 110 causes e.g. one light source 106 at a time t0 generate a light pulse and measures, in time-resolved manner, the returned scattered light by means of the light detectors 108.

For example, at least one light detector 108 measures the light at the same wavelength as the light source, thereby detecting elastic scattering. Several others of the light detectors 108 measure the light at different wavelengths from the light source, thereby detecting inelastic Raman scattering.

More details on the method of measurement and on the hardware are provided in the next sections.

Method of Measurement

As mentioned, control unit 110 is adapted to generate a series of light pulses by means of one or more light sources 106 and to measure a time-resolved scattering response from tissue 102 at several wavelengths by means of the light detectors 108.

FIG. 4 shows a single such light pulse P and the response R measured by a detector 108 as a function of time t. Typically, the light will be scattered differently from different structures 116 in the tissue 102, and the scattered light will arrive at detector 108 at different times, which gives rise to a multi-peak response as shown.

As mentioned above, at least some of the responses are obtained at wavelengths different from the illumination band $\lambda_i$. They are called the "first responses" $R1(\lambda_k, t)$, and they are measured for a plurality of different wavelengths (detection bands) $\lambda_k$ with k=1 . . . K.

At least some of the responses are obtained at the same wavelength as the illumination band. They are called the "second responses" $R2(t)$.

The first responses $R1(\lambda_k, t)$ describe the Raman spectrum at the wavelengths $\lambda_k$ over time. The second responses $R2(t)$ describe the elastic scattering over time.

Both, the first and the second responses, may contain peaks as shown in FIG. 4. In somewhat simplified terms, the locations of the peeks correspond to the "time of flight" t1, t2, t3 of light between the light source 106 via the scattering centers to the light detector 108. Since the spatial relation between light source 106 and light detector 108 is known, this allows to gain information about the location of the possible sites of the scattering centers. By combining measurements from different light sources 106 and/or light detectors 108, the location, size, and volume of the scattering centers can be determined.

Techniques for determining the location, size, and volume of structures in respect to light sources and light detectors from time-resolved elastic scattering measurements are e.g. described in Torricelli et al. in NeuroImage 85 (2014) 28-50 (http://doi.org/10.1016/j.neuroimage.2013.05.106): This document describes spatially resolved imaging using time-domain near infrared spectroscopy (TD-NIRS).

Lacarenza et al. in Biomedical Optics Express, Vol. 11, pp. 5934ff (2020) (https://doi.org/10.1364/BOE.403327): This document describes the application of time-domain near infrared spectroscopy (TD-NIRS) for detecting responses from different depth layers in the tissue.

Spatially resolved measurements can also be obtained from inelastic Raman scattering, see e.g. Iping Petterson et al, Analyst, 2010, 135, 3255-3259 (https://doi.org/10.1039/C0AN00611D).

The "echo" or response measurement between one light source and one light detector corresponds to a single "A-scan" ("A-mode"), and combining a plurality of such A-scans carried out by light sources and/or light detectors at different locations can be used to compose a spatially resolved "B-scan" ("B-mode") or "C-scan" ("C mode"). Techniques for doing this are well known from various echo probing applications, such as from ultrasonic probing and radar probing technologies. For examples, see e.g. https://en.wikipedia.org/w/ index.php?title=Medical_ultrasound&oldid=1033815201 and the references cited therein.

Hence, using these techniques, the locations (including shape and volume) of structures in tissue 102 can be identified from both the elastic as well as the inelastic scattering responses.

Advantageously, however, such locations are determined using elastic scattering because elastic scattering returns stronger signals.

In order to spatially locate structures S1, S2, S3 in the tissue, as shown, using elastic scattering, several second responses need to be recorded using light sources 106 and/or light detectors 108 at different locations. For example, FIG. 5 illustrates a measurement where a light pulse is generated by a light source 106 and the second responses are recorded by several light detectors 108 at different locations. Then, the techniques above can be used to convert the individual A-scans (responses) into a spatial representation of the individual scattering centers S1, S2, S3. For each scattering center, the location, volume, and/or shape can be determined.

Concurrently to recording the second responses as illustrated in FIG. 5, or at a different time, the first responses can be recorded. This is illustrated in FIG. 6, where it is assumed that the same light source 106 is used for recording the first responses. Further, it is assumed, for simplicity, that all light detectors 108 for recording the second first responses $R1(\lambda_k, t)$ at the various wavelengths $\lambda_k$ are placed at substantially the same location.

In that case, the first responses may e.g. look as shown in FIG. 7. Three peeks may be observed corresponding to the three structures S1, S2, and S3, respectively. Since the locations of the structures S1, S2, S3 are known from analyzing the second responses, the peeks in FIG. 7 can be attributed to the individual structures.

For each structure, a Raman spectrum for the wavelengths $\lambda_1$, $\lambda_2$, $\lambda_3$ can be obtained by identifying the sub-volume of tissue 102 corresponding to the structure and then determine a time range in the first responses that corresponds to the time-of-flight of light from light source 106 via the structure to the respective light detector 108.

FIGS. 6 and 7 illustrates a simple approach to determine the time range T2A . . . T2B attributed to structure S2. In this approach, the lengths LA and LB of the shortest path and the longest path from light source 106 via structure S2 to light detector 108 are determined. From this, the time range T2A . . . T2B can be calculated from $$T2A = LA \cdot n / c \qquad (1a)$$

and $$T2B = LB \cdot n / c, \qquad (1b)$$

where n is the (average) refractive index of the tissue at the respective wavelength $\lambda_k$g and c is the speed of light. LA and LB are obtained from analyzing the second responses as described above. For example, the refractive index at a wavelength of 1300 nm for is approximately 1.52 for the stratum corneum, 1.34 for the epidermis, and 1.41 for the dermis (see e.g. Lister et al. in J. of Biomedical Optics, 17(9), 090901 (2012) (https://doi.org/10.1117/1.JBO.17.9.090901).

If the structural analysis of the tissue from the second responses indicates that the light travels through media of different refractive index between light source 106, structure S2, and light detector 108, Eqs. (1a, 1b) can be replaced by sums of individual path sections or by integrals.

Once the time range T2A . . . T2B has been determined, the Raman spectrum attributed to structure S2 can be obtained from the first responses. For example, the Raman scattering at the wavelengths $\lambda_1$, $\lambda_2$, $\lambda_3$ can be determined by integrating (in weighted or non-weighed manner) the responses $R1(\lambda_k, t)$ between the times T2A and T2B. For example, the integral may be weighted by with $R2(t)$, thereby accounting for the scattering strength or density of different parts of the structure, i.e. parameters $p2(\lambda_k)$ for structure S2 proportional to the following integral may be calculated:

$$\int_{T2A}^{T2B} R1(\lambda_k, t) \cdot R2(t)dt \qquad (2)$$

In this way, the Raman spectrum from a specific structure (sub-volume) of the tissue can be obtained rather than an averaged, hard-to-interpret Raman spectrum of the whole tissue.

The Raman spectrum may then e.g. allow to calculate an estimate of an amount A2 of a given analyte in structure S2.

Hence, in more general terms, the present method comprises at least the following steps:

Identifying, using at least the second responses (i.e. the elastic scattering responses), a sub-volume of the tissue (such as structure S2).

Determining a time range (in the above example, this is the time range T2A . . . T2B) in the first responses $R1(\lambda_k, t)$ attributed to scattering from the identified sub-volume.

Deriving a set of parameters (such as the Raman scattering at the wavelengths $\lambda_1$, $\lambda_2$, $\lambda_3$) indicative of the first responses $R1(\lambda_k, t)$ in this time range, The individual parameters derived in the third step advantageously comprise different parameters for the first detection bands $\lambda_k$, e.g. such as the parameters $p(\lambda_k)$ derived from Eq. (2) above.

Figure 8:
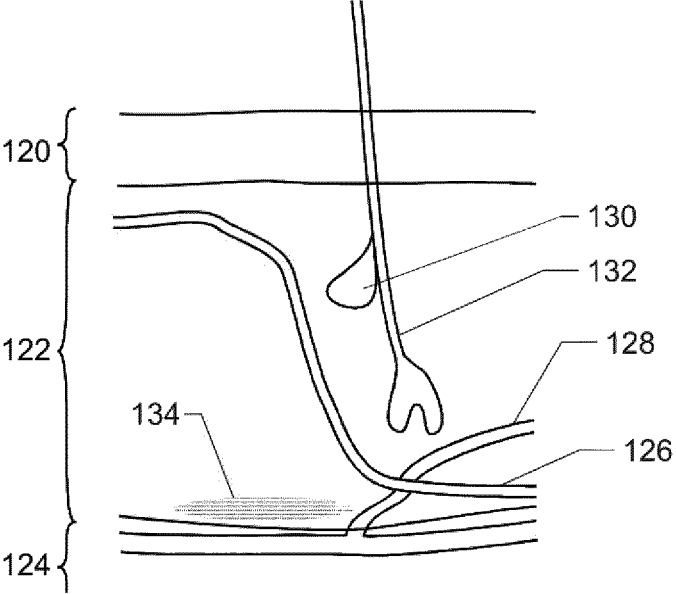
FIG. 8 is a sectional view of skin tissue with some structures that may be identified.

FIG. 8 shows a sectional view of skin tissue with some structures that might be identified as sub-volumes (structures) of interest. They may include:

The epidermis layer 120.

The dermis layer 122.

The subcutaneous tissue or subcutaneous layer 124.

Blood vessels, in particular veins 126 and arteries 128.

Glands 130.

Hair structures 132.

Interstitial fluid 134.

The present method may further comprise calculating a volume parameter indicative of the volume of a structure (sub-volume) S1, S2, S3 of interest. This allows to scale a returned first or second response signal in the time-range of the given structure by the volume of the structure.

For example, the volume of structure S2 in the example above can be estimated from the second responses to be V2. Then, the parameters $p2(\lambda_k)$ of structure S2 or the amount A2 of a given analyte at structure S2 can be scaled with I/V2, which allows to derive a concentration parameter C2 indicative of the concentration of the analyte at structure S2:

$$C2 = A2 / V2 \qquad (3)$$

In more general terms, therefore, the method may include at least the following steps:

Calculating a volume parameter (the parameter V2 in the example above) indicative of a volume of the sub-volume (i.e. of the structure S2); and Deriving a concentration parameter (C2 in the example above) indicative of the concentration of an analyte from the first responses in the time range (here: T2A . . . T2B) and from the volume parameter V2.

In the second step, it is assumed that the concentration parameter is derived from the first responses, i.e. from the Raman data. In addition or alternatively thereto, the concentration parameter may also be derived from elastic scattering, i.e. from the second responses, as described in more detail below. Hence, in more general terms, the concentration parameter may be derived from the first and/or the second responses in the time range and from the volume parameter V2.

As mentioned, the first responses $R1(\lambda_k, t)$, i.e. the Raman spectra, may be used for assessing the amount of an analyte in a structure of interest.

For example, as described by Kang et al., Sic. Adv. 2020; 6, pp. 1-8 (https://doi.org/10.1126/sciadv.aay5206), glucose may be detected from its specific Raman fingerprint.

Similarly, as described by Huang et al. in J. of Biomedical Optics, 9(6), (2004), pp. 1198ff(https://doi.org/10.1117/1.1805553), cutaneous melanin can also be detected from its Raman spectrum.

In addition to or alternatively to measuring analytes by means of their Raman spectra, analytes can also be determined by measuring elastic scattering at several wavelengths.

To do so, the second responses R2 must be measured at several illumination wavelengths L, with n=1 to N and N>1. The second responses $R2(t, \lambda_n)$ measured in that way can then not only be used to locate structures within the tissue but also to assess their composition.

Further, measuring the second responses $R2(t, \lambda_n)$ for a plurality of illumination wavelengths $\lambda_n$ adds additional data to be used for locating structures in the tissue. In particular, light at a wavelength range between 1200 and 1700 nm is only weakly absorbed by skin tissue and therefore can reach deep structures, while light at a wavelength range between 500 and 1200 nm is more strongly scattered and can provide a more detailed mapping of structures in the upper regions of the skin tissue.

Figure 9:
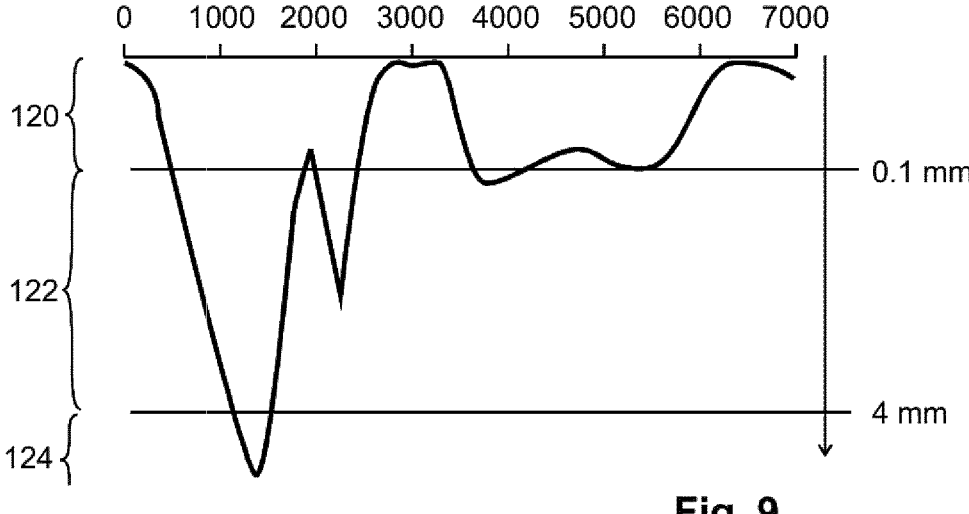
FIG. 9 shows the penetration depth of light into tissue as a function of wavelength.

This is illustrated by FIG. 9, which shows the penetration depth of light into tissue (95% absorption) as a function of wavelength.

Hence, in more general terms, the method advantageously comprises the step of measuring the second responses $R2(t, \lambda_n)$ for a plurality of different illumination bands (i.e. wavelengths $\lambda_n$). In particular, the different illumination bands should be non-overlapping. Advantageously, at least some of them differ by more than 100 nm.

In particular, at least one of the illumination bands is within the range of 1200 to 1700 nm. Advantageously, several of the illumination bands are within this wavelength range.

As to detecting analytes by means of elastic scattering, i.e. form the second responses $R2(t, \lambda_n)$, various analytes can be determined if the second responses are carried out at different wavelengths. For example:

Blood oxygenation (i.e. the concentration of oxygenated hemoglobin and deoxygenated hemoglobin or the ratio of their concentrations) can be calculated from the elastic scattering strengths at two wavelength e.g. at 670 nm and 830 nm, see e.g. Lacerenza it al. in Biomedical Optics Express, 11(10), pp. 5934ff (2020), /https://doi.org/10.1364/BOE.403327).

Measurement of stress biomarkers in different bodily fluids (e.g., cortisol or dopamine in plasma) by using UV absorption (Ray et alt in ACS Sensors 2019, 4, 1346-1357, DOI: 10.1021/acssensors.9b00301)

In addition to the first and second responses described above, the present device may also measure at least one additional parameter by means of additional sensors and/or data processing units $109a$-$109g$ as illustrated in FIG. 3. These additional parameters may include:

A temperature parameter: This parameter depends on the temperature of the tissue. It may e.g. be measured by a temperature sensor 109$a$.

A hydration parameter: This parameter depends on the hydration (water content) of the tissue. It can be measured by a hydration sensor 109$b$. This sensor may e.g. measure skin conductance. Various techniques are e.g. described by Qassem et al. in Cosmetics 2019(6), 19 (https://doi.org/10.3390/cosmetics6010019).

A sun exposure parameter: This parameter depends on the current sun exposure of the tissue. It can be measured by a sun exposure sensor 109$c$. In particular, it can be measured by means of a signal indicative of the UV radiation intensity at the tissue. For this purpose, sun exposure sensor 109$c$ may comprise a UV sensor.

An activity parameter: This parameter depends on the physical activity of the subject. In particular, it may be measured by means of an acceleration sensor 109$d$. The activity parameter may e.g. be derived from an average of the absolute acceleration measured over a certain period of time.

A fluorescence parameter: This parameter depends on the fluorescent response of the tissue to the light pulses. It may be measured by means of a fluorescence unit 109$e$. Such a unit may e.g. be implemented in software and use the signals of the light detectors 108 but evaluate them at least 1 nanosecond or later after the light pulse. At these times, the signals received are not due to elastic or inelastic scattering but due to fluorescence.

Further sensors and or data processing units 109$f$, 109$g$ may measure other parameters.

All these additional parameters affect the concentration of certain analytes in the tissue. For example, activity affects blood oxygenation and glucose. Temperature affects the amount of blood and water in the tissue.

They may be used to further refine the results obtained from the present device.

Such additional parameters may be measured, at least in part, by the light sources 106 and light detectors 108 described above. However, the device may also include different light sources or light detectors, e.g. with wider FWHM, such as LEDs or such as photodiodes without filters.

In one embodiment, control unit 110 may comprise a neural network 111, which receives parameters derived from the first and/or second responses as well as the additional parameters as its inputs.

Neural network 111 may comprise a classifier trained to classify its input parameters to detect various critical states, such as hypoglycemia and/or hyperglycemia, dehydration, shock, overheating, etc.

In another embodiment, neuronal network 111 may e.g. comprise regression neural network providing estimates of the concentration or amount of certain analytes.

Deep Detection

One challenge when measuring structures deep within the tissue is the significant absorption of radiation even in the near infrared (cf. FIG. 9). This renders scattering signals coming from the upper tissue regions much stronger than those coming from the tissue skin regions.

Figure 12:
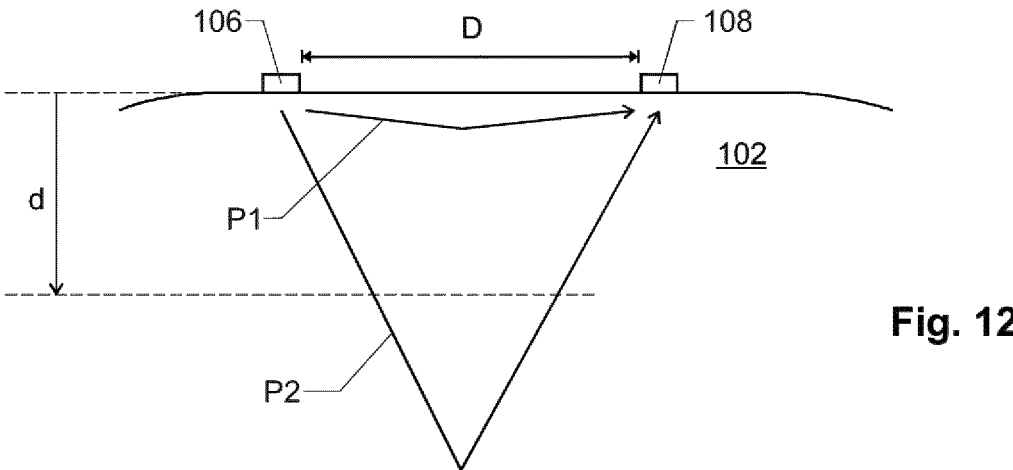
FIG. 12 illustrates shallow vs. deep scattering.

This is illustrated in FIG. 12, where a shallow scattering path P1 and a deep scattering path P2 are shown between a given light source 106 and a light detector 108. Since shallow path P1 is considerably shorter than deep path P2, it suffers much less absorption and will lead to a significantly stronger signal at detector 108.

However, the signal originating from deep path P2 can be isolated from the one of shallow path P1 in the time domain. This is explained in the following.

The shortest path P2 extending into depth d has a total optical length L of approximately $$L = 2 \cdot n \cdot \sqrt{d^2 + D^2/4}, \tag{4}$$

with D being the distance between light emitter 106 and light detector 108 and n being the (average) refractive index of the tissue.

Hence, the earliest time te at which a signal from a depth d is expected at detector 108 after the start of a given light pulse from light source 106 is $$te = \frac{2 \cdot n}{c} \cdot \sqrt{d^2 + D^2/4}, \tag{5}$$

wherein c is the speed of light.

In particular, d should be chosen to be at least 2 mm, in particular at least 3 mm, in particular at least 4 mm. This will allow to reach the deeper tissue levels, in particular skin levels, that light can still reach.

In more general terms, the method advantageously comprises the steps of emitting a light pulse by means of the light source 106 at a start time t0, detecting one of the first responses and/or the second response at a given light detector 108, and deriving the information on the tissue using a time sub-range in the response at the given light detector 108 that starts at an earliest time te after the start time t0, with $$te > \frac{2 \cdot n}{c} \cdot \sqrt{d^2 + D^2/4}, \tag{6}$$

with n being at least 1.3, c being the speed of light, D being the distance between the light source and the given light detector, and d being at least 2 mm, in particular at least 3 mm, in particular at least 4 mm.

For example, if D is assumed to be 4 mm, te should be at least 18 ps, 19 ps, 20 ps, 27 ps, or 36 ps for d being at least 0.5 mm, 1 mm, 2 mm, at least 3 mm, or at least 4 mm.

For distinguishing scattered photons from regions closer to the surface, the distance D should advantageously be smaller. For example, if D is 1 mm, te for d=0.5 mm and 1 mm will differ more strongly, with te(d=0.5 mm)=6 ps and te(d=1 mm)=10 ps.

Hence, advantageously, the distance D between at least one of the light sources 106 and at least one of the light detectors 108 is less than 2 mm, in particular less than 1 mm.

This allows to better distinguish light scattered from different depths d below a few mm.

These steps allow to filter out major disturbances from the strong signals due to shallow scattering.

Temporal Resolution

As mentioned, the responses should be measured with a temporal resolution better than 40 ps, advantageously better than 20 ps, in particular better than 10 ps. This is based on the fact that structures of interest in the tissue should advantageously be resolved with a resolution of no more than a few millimeters. For example, when measuring a structure of interest of a depth of 4 mm, in backscattering, the photons scattered from its top and bottom surface will approximately see a path different of 8 mmi Assuming that the refractive index is around 1.5, this corresponds to a time difference of 40 ps. Some structures, such as individual skin layers, may have smaller extensions of e.g. 2 mm or 1 mm, and blood vessels may also have extensions in the millimeter or sub-millimeter regime, which would correspond to time differences of 20 ps and 10 ps, respectively.

Measuring the scattering responses in time-resolved manner with such a temporal resolution allows to perform time-of-flight measurements that allow to assess the location and/or extension of the scattering centers 116 of the tissue 102 in respect to the respective light source 106 and light detector 108 with the spatial resolution mentioned above.

Hardware

As mentioned, the present device comprises an array of fast, sensitive light detectors 108, advantageously SPADs.

The light detectors 108 may be arranged on a single substrate 140 (see FIG. 1), in particular on a semiconductor chip, advantageously together with the light sources 106.

Figure 10:
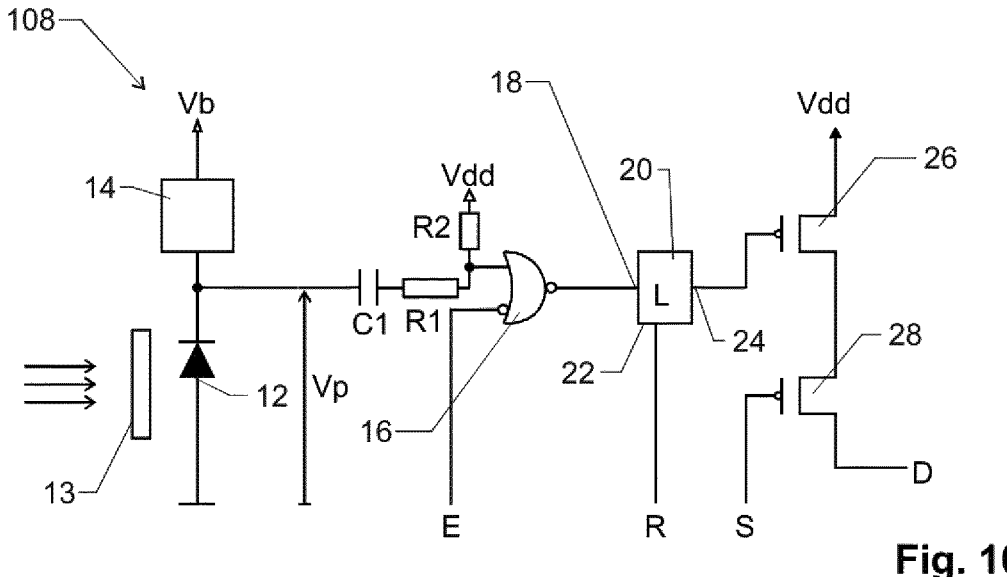
FIG. 10 shows a circuit diagram of a light detector.

At least the detectors 108 for measuring the first responses should be narrow-band light detectors. Advantageously, they comprise a single-photon avalanche diode 12 and an optical bandpass filter 13 as shown in FIG. 10.

Bandpass filter 13 may e.g. comprise a dielectric interference filter comprising several thin layers of different refractive index. It may also comprise a diffractive grating, such as a zero-order diffractive grating. Both these structures can be used to manufacture filters of narrow transmission width, FIG. 10 shows an example of one light detector 108 in an array of light detectors. It comprises the single-photon avalanche diode 12 in series with a quenching circuit 14.

A reverse-voltage is applied over diode 12 as known to the skilled person. Quenching circuit 14 is adapted to apply a voltage close to or slightly above the breakdown voltage. When a photon arrives at diode 12, an electron-hole pair is released and a current starts to flow, which generates an avalanche effect. The rising current leads to an increase of the voltage drop over quenching circuit 14 and thereby to a decrease of the voltage over diode 12. Quenching circuit 14 is dimensioned and structured to let the voltage over diode 12 drop below its critical voltage, thereby quenching the current.

In a simple embodiment, quenching circuit 14 can be a resistor. Alternatively, quenching circuit 14 may be an active circuit that generates a non-linearly increasing voltage vs. current or a voltage drop that increases over time in order to more quickly quench the current in diode 12.

In the shown embodiment, the anode of diode 12 is applied to ground and the voltage applied at its cathode is positive in respect to ground. Hence, the voltage Vp at its cathode is positive. When a photon arrives, the voltage Vp temporarily decreases.

The voltage Vp over diode 12 is sent through a capacitor C1 and a resistor R1 to a gate 16.

The second input of gate 16, which is a NOR gate, is an enable signal E. Only while E is set to 1, a pulse coming from diode 12 will be propagated through gate 16.

The output of gate 16 is applied to the signal input 18 of a one bit latch 20. Latch 20 is set to its on-state by a signal from diode 12.

Latch 20 further comprises a reset input 22, which is connected to a reset input R of cell 10. An active signal at reset input 22 sets latch 20 into its off-state.

The output 24 of latch 20 is applied to the control input (or gate) of a first switch (in particular a first transistor) 26. First switch 26 is arranged in series to a second switch (in particular a second transistor) 28. Second switch 28 is controlled by means of a readout input S of cell 10.

The two switches 26, 28 connect a fixed-voltage potential Vdd (or a current source) to a digital output D of cell 10.

Second switch 28 forms a readout circuit for enabling digital output D. If the signal at readout input S is disabled, digital output D is in high impedance. Otherwise, the state of digital output D depends on the state of latch 20. This allows to tie several of the circuits of FIG. 10 to a single read-out bus, which can be queried by control unit 110.

Figure 11:
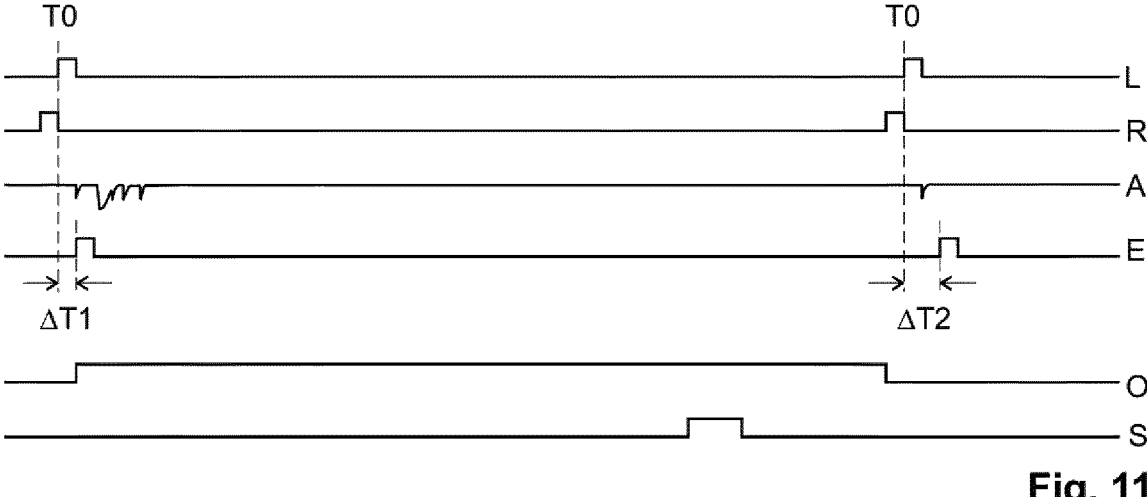
FIG. 11 is a timing diagram for operating the light detector.

Operation of the circuit of FIG. 10 is illustrated in FIG. 11.

Control unit 110 is adapted to carry out repetitive measurement cycles, with each measurement starting at time TO. At this time, control unit 110 sends a signal L to light source 106 for emitting a short light pulse.

As scattered photons arrive at light diode 12, they generate an analog signal A (which corresponds to the voltage Vp mentioned above).

Control unit 110 uses enable input E to select a time window for sampling the signal from photodiode 12. In the first measurement cycle of FIG. 11, it sets enable signal E to 1 for a short time period at a time $\Delta T1$ after the start of the cycle. In the second measurement cycle of FIG. 11, it sets enable signal E to 1 at a later time $\Delta T2$, etc.

If a photon was detected while enable signal E was 1, latch L is set to 1, as shown by signal O in FIG. 11.

At the end of the cycle, control unit 110 reads out the contents of latch 22 by connecting the output of latch L to the read-out bus by setting readout input S to 1.

FIG. 10 is but an example of a detector circuit. Other designs are known to the skilled person, see e.g. Conca et al. in IEEE Journal of Solid-State Circuits, 55(11), pp. 3097ff (2020) (https://doi.org/10.1109/JSSC.2020.3006442).

The cycles of FIG. 11 are repeated for different time windows, thereby obtaining the first and second time-resolved responses.

Light detectors 108 with the circuitry of FIG. 10 can e.g. be arranged in a two-dimensional array, with the outputs D of each row connected to a common row bus line. Control unit 110 may in this case be adapted to generate suitable timing signals the for enable inputs E as described above. For each light pulse, it can then read out the results for each row bus line by sequentially activating the light detectors connected to the given row bus line by means of timed readout signal S.

In the array of light detectors, different filters 13 (i.e. filters for different wavelengths) can be attributed to the light detectors for obtaining responses at the wavelengths $\lambda_n$ and $\lambda_k$.

NOTES

In the example above, the first and second responses have been combined by first identifying a sub-volume from at least the second response, by determining the time range in the responses corresponding to the sub-volume, and then by deriving information using the responses in the time range.

Alternatively, or in addition thereto, the first and second responses may e.g. be combined by selecting a suitable time range corresponding e.g. to a typical tissue layer, e.g. the dermis. Then, the responses in this time range may be combined.

The same light sources 106 and/or detectors 108 may be used to measure the first as well as the second responses. Alternatively, at least one light source and/or at least one detector may be used to measure only the first responses or only the second responses.

In the embodiments above, the light detectors are based on SPADs for high sensitivity. It must be noted, though, that other detection techniques can be used as well, such as simple photodiodes, in particular if sufficiently strong light sources are used.

In the embodiment of FIG. 1, the shown device has a single substrate 140. The present device may also include several such substrates 140 at different locations on the tissue for obtaining better spatial resolution.

While there are shown and described presently preferred embodiments of the invention, it is to be distinctly understood that the invention is not limited thereto but may be otherwise variously embodied and practiced within the scope of the following claims.

The invention claimed is:

1. A method for a spatially-resolved probing of biological tissue comprising steps of:
emitting, by means of at least one light source, a series of light pulses into the tissue;
measuring, by means of a plurality of light detectors, a plurality of time-resolved responses to the light pulses scattered from the tissue with a temporal resolution better than 40 ps, wherein
a plurality of first responses is in response to light pulses in a first illumination band and is measured at a plurality of first detection bands, wherein the first detection bands differ from each other and from the first illumination band, and
a plurality of second responses is in response to light pulses in a second illumination band and is measured at a second detection band, wherein the second detection band overlaps with the second illumination band; and
deriving at least one spatially resolved tissue parameter from combining the first and the second responses by identifying, using at least the second responses, a sub-volume of the tissue;
determining a time range in the first responses attributed to scattering from the sub-volume; and
deriving a set of parameters indicative of the first responses in said time range.

2. The method of claim 1 wherein the first illumination band has a full width at half maximum of less than 5 nm.

3. The method of claim 1 wherein distances between the light source and at least some of the light detectors are less than 20 mm.

4. The method of claim 1 where the sub-volume is one of an epidermis layer, a dermis layer, a sub-cutaneous layer, a blood vessel, a gland, a hair structure, interstitial fluid.

5. The method of claim 1 comprising:
calculating a volume parameter indicative of a volume of the sub-volume; and deriving a concentration parameter indicative of a concentration of an analyte from the first and/or second responses in the time range and from the volume parameter.

6. The method of claim 1 wherein the tissue is a body surface of an animal, wherein the method comprises:
sending the light pulses through a skin layer of the animal; and
receiving the first and second responses through the skin layer.

7. The method of claim 1 comprising:
measuring the second responses for a plurality of different illumination bands.

8. The method of claim 7 wherein at least one of the illumination bands is within a wavelength range of 1200 to 1700 nm.

9. The method of claim 1 wherein the temporal resolution is better than 20 ps.

10. The method of claim 1 wherein the first detection bands have a full width at half maximum of less than 5 nm.

11. The method of claim 1 wherein distances between the light source and at least some of the light detectors are less than 1 mm.

12. A method for a spatially-resolved probing of biological tissue comprising:
emitting, by means of at least one light source, a series of light pulses into the tissue;
measuring, by means of a plurality of light detectors, a plurality of time-resolved responses to the light pulses scattered from the tissue with a temporal resolution better than 40 ps, wherein
a plurality of first responses is in response to light pulses in a first illumination band and is measured at a plurality of first detection bands, wherein the first detection bands differ from each other and from the first illumination band, and
a plurality of second responses is in response light pulses in a second illumination band and is measured at a second detection band, wherein the second detection band overlaps with the second illumination band;
deriving information on the tissue from a combination of the first and second responses; and
measuring at least one additional parameter, wherein the additional parameter is one of
a temperature parameter depending on a temperature of the tissue,
a hydration parameter depending on a hydration of the tissue,
a sun exposure parameter depending on a sun exposure of the tissue, an activity parameter, and
a fluorescence parameter depending on a response of the tissue to the light pulses measured after at least 10 nanoseconds.

13. A method for a spatially-resolved probing of biological tissue comprising:
emitting, by means of at least one light source, a series of light pulses into the tissue;
measuring, by means of a plurality of light detectors, a plurality of time-resolved responses to the light pulses scattered from the tissue with a temporal resolution better than 40 ps, wherein
a plurality of first responses is in response to light pulses in a first illumination band and is measured at a plurality of first detection bands, wherein the first detection bands differ from each other and from the first illumination band, and a plurality of second responses is in response light pulses in a second illumination band and is measured at a second detection band, wherein the second detection band overlaps with the second illumination band; and deriving information on the tissue from a combination of the first and second responses by emitting a light pulse by means of the light source at a start time t0;

detecting at least one of the first responses and/or the second response at a given light detector; and deriving the information on the tissue using a time subrange in the response at the given light detector that starts at an earliest time te after the start time t0, with $$te > \frac{2 \cdot n}{c} \cdot \sqrt{d^2 + D^2/4},$$

with n being at least 1.3, c being the speed of light, D being a distance between the light source and the given light detector, and d being at least 0.5 mm.

* * * * *